United States Patent
Codignola

(10) Patent No.: US 6,670,502 B1
(45) Date of Patent: Dec. 30, 2003

(54) PROCESS FOR THE PRODUCTION OF AROMATIC ACIDS

(76) Inventor: Franco Codignola, Corso Lodi 59, Milan (IT)

( * ) Notice: Subject to any disclaimer, the term of this patent is extended or adjusted under 35 U.S.C. 154(b) by 496 days.

(21) Appl. No.: 09/670,714

(22) Filed: Sep. 28, 2000

Related U.S. Application Data

(63) Continuation-in-part of application No. 09/331,754, filed as application No. PCT/EP97/03154 on Jun. 14, 1997, now Pat. No. 6,160,170.

(30) Foreign Application Priority Data

Dec. 27, 1996 (IT) .......................................... MI96A2753

(51) Int. Cl.[7] .............................................. C07L 51/16
(52) U.S. Cl. ...................................... 562/412; 562/409
(58) Field of Search ................................. 562/409, 412

(56) References Cited

FOREIGN PATENT DOCUMENTS

EP          026507    *    4/1981

* cited by examiner

Primary Examiner—Paul J. Killos
(74) Attorney, Agent, or Firm—Nixon & Vanderhye

(57) ABSTRACT

Process for producing mono- and poly-carboxylic aromatic acids wherein an aromatic compound having at least one oxidizable substituent directly linked to the carbon atom of the corresponding aromatic nucleus is oxidized in the presence of a catalyst system in the liquid homogenous phase. The oxidation reaction is carried out in aqueous acetic acid, and the catalyst system consists of a combination of cobalt and zirconium organic salts. The oxidation reaction is carried out at an absolute pressure lower than 10 bar and at a temperature of 90–150° C.

14 Claims, No Drawings

PROCESS FOR THE PRODUCTION OF AROMATIC ACIDS

This application is a continuation-in-part of Ser. No. 09/331,754 filed Jun. 25, 1999, now U.S. Pat. No. 6,160,170, which is a 371 of PCT/EP97/03154 filed Jun. 14, 1997.

The present invention relates to a novel process for the production of monocarboxylic and polycarboxylic aromatic acids by the catalytic oxidation in homogeneous phase of aromatic compounds carrying at least one oxidizable substituent group attached directly to the carbon atom of the corresponding aromatic nucleus.

The expression "oxidizable substituent group" is intended to indicate any substituent in which a carbon atom is bonded directly to the aromatic nucleus and which, as a result of oxidation, is converted into a carboxylic group still bonded to the aromatic ring.

The methyl, methylene, hydroxymethylene, ketone and aldehyde groups are considered to be among the more interesting oxidizable substituent groups; the aromatic compounds used as starting materials in the present invention are therefore those which possess one or more of the mentioned oxidizable substituent groups.

In order to better illustrate the invention, there will be indicated hereinafter, purely by way of non-limiting example, some of the possible oxidations which can be carried out with the present invention:

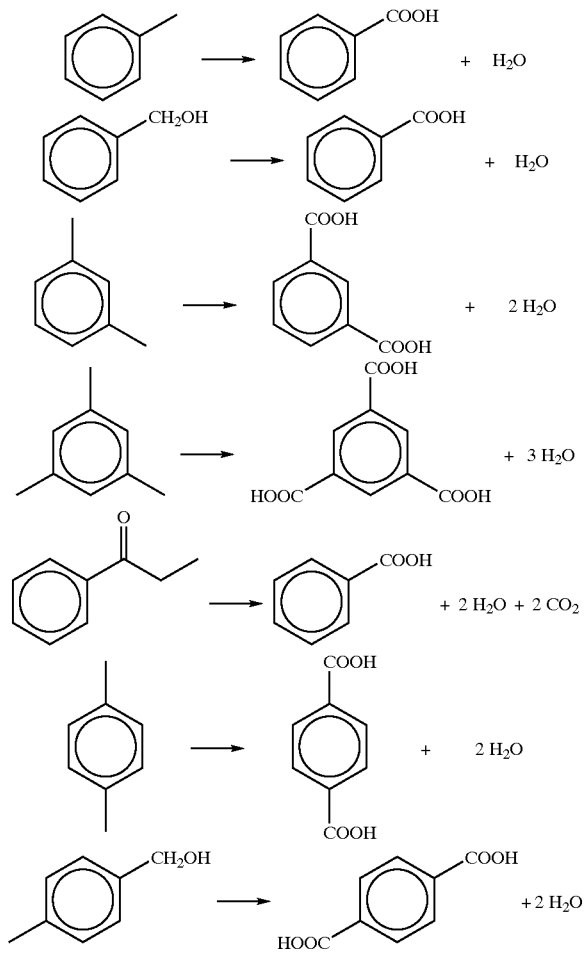

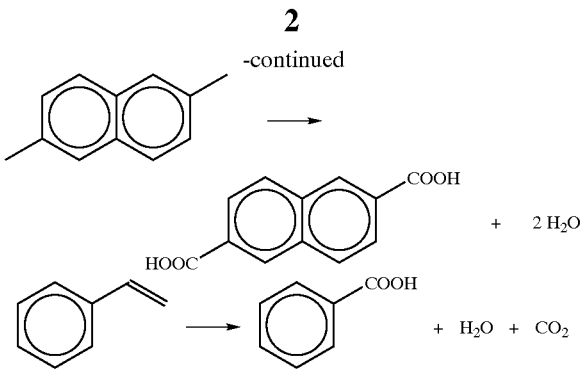

In particular, when there are two or more oxidizable groups, each of these groups has to be separated from the others by at least one carbon atom of the unsubstituted aromatic ring; with the process of the present invention it is thus not possible to oxidize o-xylene to phtalic acid, or 1,2-dimethylnaphtalene to 1,2-dinapthoic acid.

According to the prior art, the above mentioned oxidation processes are carried out in the presence of an oxidizing agent, which is generally gaseous molecular oxygen, preferably diluted with an inert gas; for obvious reasons of practicality, air (optionally enriched with molecular oxygen) is the gaseous mixture most commonly used for this purpose. The oxidation reaction is normally carried out using as solvent an aqueous organic acid, preferably acetic acid, normally with a water content of from 2 to 15%.

Those reactions are carried out in the presence of a catalytic complex generally composed of one or more metals, normally in the form of salts soluble in the reaction solvent, and a suitable activator. The metal performs the function of catalyzing the actual oxidation reaction while the activator is used to return the metal (which undergoes a reduction in its oxidation number during catalysis) to its original valency, thus enabling it to regain and exert its catalytic activity; due to its low cost and its relatively high catalytic activity, cobalt is normally the catalytic metal preferred in this art. The activator may itself be a metal, in which case it also will preferably be present in the form of a salt soluble in the reaction medium; alternatively, it is possible to use organic compounds having carbonyl functions, such as ketones or aliphatic aldehydes, preferably acetaldehyde, or molecular bromine.

U.S. Pat. No. 5,112,592 describes the production of aromatic acids at temperatures of from 100 to 275° C., using metals from groups IIIA and IVA of the periodic table of elements (groups IIIB and IVB according to the new notation adopted, for example, by Perry, *Chemical Engineers' Handbook, VI edition,* 1984), in particular zirconium and hafnium, in order to increase the kinetics of oxidation reactions that use catalytic complexes based on cobalt and manganese in the presence of bromine as the activator.

European patent application EP-475926 describes a process for the production of polycarboxylic aromatic acids which uses a catalytic complex based on manganese and cobalt and which operates at temperatures of from 100 to 220° C. and at pressures of 100 kilopascals or higher.

The above listed documents all relate to oxidation processes carried out in presence of non metallic activators, such as aldehydes, ketones or bromine, which are of difficult industrial handling and/or are consumed in large amounts. The activating action of bromine, in particular, takes place at temperatures of about 150 to 250° C. and at pressures of at least 20–25 bar; consequently, given the high operating conditions, the corresponding plants have to be constructed with particularly resistant materials, such as titanium or its alloys, with an evident increase in costs.

Finally, U.S. Pat. No. 3,299,125 discloses a process for the production of aromatic acids by catalytic oxidation of the corresponding aromatic precursor in presence of a catalyst system containing (A) at least one metal selected from the groups IIIA and IVA of the periodic table, preferably scandium, yttrium, lanthanum, neodymium, gadolinium, thorium, zirconium or hafnium, and (B) cobalt. Although the mentioned process can be operated in absence of non metallic activators, such as aldehydes, ketones or bromine, the reported yields are however very low and deprived therefore of any industrial interest; in particular, it must be observed that yields of about 80% are achieved only if the absolute reaction pressure is higher than 20 bar or if a third metal catalyst is added to the reaction mixture and pure molecular oxygen is used as the oxygen source.

The aim of the present invention is therefore to provide a new process for the manufacture of aromatic acids which is free from all the disadvantages mentioned above and, in particular, a process which can be carried out at low pressures and temperatures, in presence of a cobalt-based catalyst and in absence of non metallic activators.

A process has now surprisingly been found, and constitutes the subject-matter of the present invention, for the oxidation of aromatic compounds containing at least one oxidizable substituent group directly attached to the carbon atom of the corresponding aromatic ring in which the aromatic compound is reacted with molecular oxygen and/or air in presence of a catalyst system in liquid homogeneous phase, said catalyst system consisting of cobalt and zirconium organic salts and the oxidation reaction being carried out at an absolute pressure lower than 10 bar and at a temperature of 90–150° C.

As it will be demonstrated in the attached examples, the combination of elements according to the present invention, namely a catalyst system based on cobalt and zirconium organic salts, a temperature reaction of 90–150° C. and an absolute pressure reaction lower than 10 bar, is capable of catalyzing almost completely the oxidation of aromatic compounds containing at least one oxidizable substituent group to give the corresponding aromatic acids without the necessity for the use of non-metallic activators.

More in details, the process according to the present invention is preferably carried out at a temperature of 100–120° C. and at an absolute pressure of from 1 to 6 bar, even more preferably at an absolute pressure of from 2 to 5 bar.

The cobalt and zirconium organic salts are normally acetates; in particular, the weight ratio between the cobalt acetate and the zirconium acetate is generally comprised between 1:1 and 1:0.01 and, more preferably, it is of about 1:0.3, whereas the amount of the zirconium acetate is normally of 0.05–1 gram atom/gram mole of the aromatic compounds to be oxidized to the corresponding carboxylic acids.

The reaction solvent is normally constituted by C1–C6 aliphatic acids or mixtures thereof, preferably aqueous acetic acid; normally, the aqueous acetic acid is used in a concentration comprised between 85 and 98% by weight and, preferably, in a concentration comprised between 95 and 98% by weight.

The oxidizable aromatic precursors are normally selected from the group consisting of toluene, p-xylene, m-xylene, mesitylene and 2,6-dimethyl-naphtalene.

According to its best realization, the present invention consists of a process for the production of mono- and poly-carboxylic aromatic acids wherein an aromatic oxidizable precursor is oxidized with air, optionally enriched with molecular oxygen, in presence of a catalyst system consisting of cobalt acetate and zirconium acetate in a weight ratio of about 1:0.3, the oxidation reaction being carried out in aqueous acetic acid at an absolute pressure of from 2 to 5 bar and at a temperature of 100–120° C.

Those and other aspects of the invention are indicated in the following examples which are to be regarded as non-limiting illustrations of the invention.

EXAMPLE 1

The reaction is carried out in a round-bottomed flask, equipped with a magnetic stirrer, an heating-cooling bath by means of a circulation of a mixture of water and diethylene glycol mixture, and a oxygen-meter. The oxidation is carried with oxygen at an absolute pressure of 1.01 bar and at a temperature of 100° C. The reaction mixture has the following composition:

Co (II): 0.01 mole

Zr: 1.45 mmole p-xylene: 0.1 mole

An induction time of 5–6 hours is observed. After 5 hours, after the induction period, the theoretical yield is higher than 90%.

EXAMPLE 2

The reaction is carried out in a 6 liter autoclave, equipped with a turbine agitator with a fixed rotation speed of 1,300 rounds per minute, an heating-cooling bath by means of a circulation of a diathermic liquid. Instead of oxygen, the oxidizing agent is air. The oxidation is carried at an absolute pressure of 2 bar and at 115–120° C. The reaction mixture has the following composition:

acetic acid: 2,650 g p-xylene: 490 g $Co(OAc)_2 4 H_2O$: 120 g $Zr(OAc)_2$: 12 g An induction time of 5 hours is observed. A loss of 19 g of p-xylene in the vent gas has been observed.

After 5 hours, after the induction period, the theoretical yield on converted p-xylene is 92.9%.

EXAMPLE 3

The procedure is the same of example 2, but the absolute pressure is 4 bar.

An induction time of 3 hours is observed. A loss of 10 g of p-xylene in the vent gas has been observed.

After 5 hours, after the induction period, the theoretical yield on converted p-xylene is 93.9%.

EXAMPLE 4

The procedure is the same of example 2, but the absolute pressure is 6 bar.

An induction time of 1.7 hours is observed. A loss of 5.7 g of p-xylene in the vent gas has been observed.

After 5 hours, after the induction period, the theoretical yield on converted p-xylene is 94%.

What is claimed is:

1. A process for the production of mono- and poly-carboxylic aromatic acids wherein an aromatic compound bearing at least one oxidizable substituent group directly linked to the carbon atom of the corresponding aromatic nucleus is oxidized in presence of a catalyst system in liquid homogeneous phase, wherein said catalyst system consists of a combination of cobalt and zirconium organic salts and the oxidation reaction is carried out in aqueous acetic acid at an absolute pressure lower than 10 bar and at a temperature of 90–150° C.

2. A process according to claim 1 wherein the oxidation reaction is carried out at a temperature of 100–120° C.

3. A process according to claim 1 wherein the oxidation reaction is carried out at an absolute pressure of from 1 to 6 bar.

4. A process according to claim 3 wherein the oxidation reaction is carried out at an absolute pressure of from 2 to 5 bar.

5. A process according to claim 1 wherein said cobalt and zirconium organic salts are acetates.

6. A process according to claim 5 wherein the weight ratio between the cobalt acetate and the zirconium acetate is comprised between 1:1 and 1:0.01.

7. A process according to claim 6 wherein said weight ratio is 1:0.3.

8. A process according to claim 5 wherein the amount in the reaction mixture of the zirconium acetate is of 0.05–1 gram atom/gram mole of the aromatic compounds to be oxidized to the corresponding carboxy acids.

9. A process according to claim 1 wherein the aqueous acetic acid is used in a concentration comprised between 85 and 98% by weight.

10. A process according to claim 9 wherein the aqueous acetic acid is used in a concentration comprised between 95 and 98% by weight.

11. A process according to claim 1 wherein the oxidation is carried out with air.

12. A process according to claim 1 wherein said aromatic compound bearing at least one oxidizable substituent group directly linked to the carbon atom of the corresponding aromatic nucleus is selected from the group consisting of toluene, p-xylene, m-xylene, mesitylene and 2,6-dimethyl-naphtalene.

13. A process according to claim 1 wherein the process is carried out in the absence of non-metallic activators.

14. A process according to claim 11 wherein the air is enriched with molecular oxygen.

* * * * *